United States Patent [19]
Sehgal et al.

[11] 3,983,231
[45] Sept. 28, 1976

[54] ANTIBIOTIC SUBSTANCES AND PREPARATION

[75] Inventors: Surendra N. Sehgal, Dollard des Ormeaux; Kartar Singh, Beaconsfield; Claude Vezina, Deux-Montagnes, all of Canada

[73] Assignee: Ayerst McKenna and Harrison Ltd., Montreal, Canada

[22] Filed: June 26, 1975

[21] Appl. No.: 590,542

Related U.S. Application Data

[60] Division of Ser. No. 467,167, May 6, 1974, Pat. No. 3,911,112, which is a continuation-in-part of Ser. No. 377,985, June 10, 1973, abandoned.

[52] U.S. Cl. ............................ 424/118; 424/115; 424/116
[51] Int. Cl.² ........................................ A61K 35/74
[58] Field of Search .................. 424/118, 116, 115

[56] References Cited
OTHER PUBLICATIONS
Miller, The Pfizer Handbook of Microbial Metabolites, McGraw-Hill Book Co., Inc., N.Y., N.Y., 1961, pp. 578–580.

*Primary Examiner*—Jerome D. Goldberg

[57] ABSTRACT

A new antibiotic complex, complex 484, components 484-A and 484-B thereof and a process for their preparation are disclosed. These antibiotic substances are producible by culturing a microorganism of the species Streptomyces in an aqueous nutrient medium under submerged aerobic fermentation conditions. The substances are useful against a broad spectrum of pathogenic bacteria. Methods for their use are disclosed also.

4 Claims, 3 Drawing Figures

Figure 1:
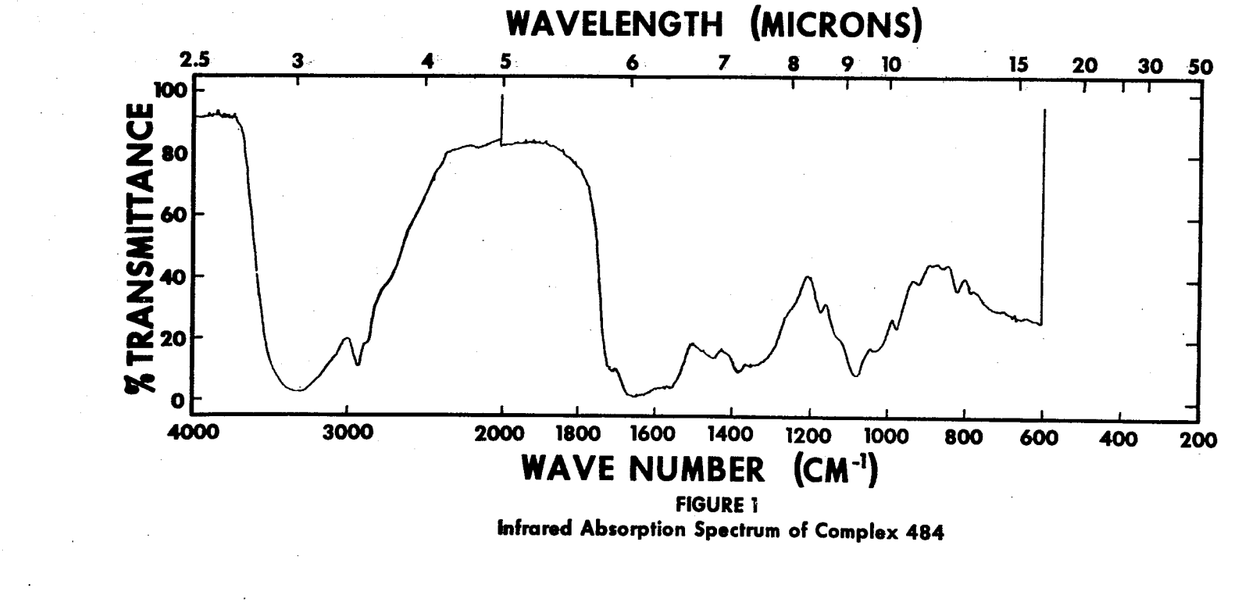

FIGURE 1
Infrared Absorption Spectrum of Complex 484

Figure 2:
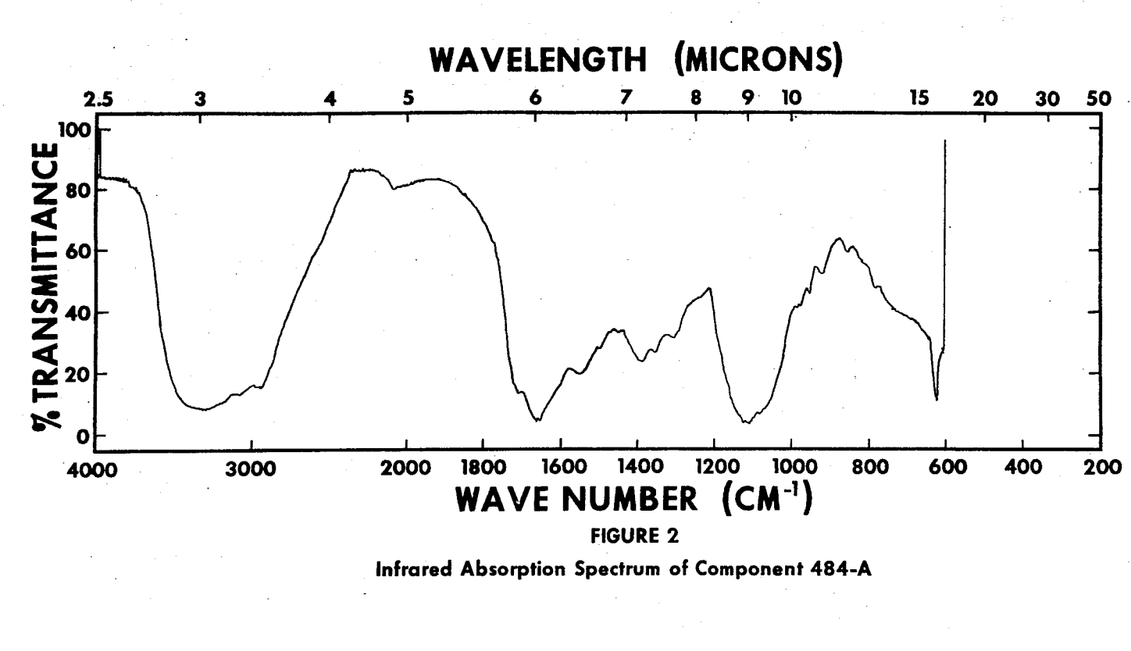

FIGURE 2
Infrared Absorption Spectrum of Component 484-A

ANTIBIOTIC SUBSTANCES AND PREPARATION

The application is a division of application Ser. No. 467,167, filed May 6, 1974, now U.S. Pat. No. 3,911,112, issued Oct. 7, 1975, which latter application is a continuation-in-part of Ser. No. 377,985, filed June 10, 1973, and now abandoned.

BACKGROUND OF THE INVENTION a. Field of Invention

This invention relates to new antibiotic substances and to a process for producing them. More specifically, this invention relates to an antibiotic complex designated herein as "complex 484" and to individual antibiotic components thereof.

b. Description of the Prior Art

The antibiotic complex of this invention and certain of the components thereof generally resemble those of the streptothricin family of antibiotics but obvious differences do exist as indicated by chromatography and by the products obtained on hydrolysis. More particularly, the isolation of the base streptolidine and the amino acid L-$\beta$-lysine following acid hydrolysis of the antibiotic substances of this invention strongly suggests that the present antibiotic substances are related to the streptothricin family. See for example streptothricin, S. A. Waksman and H. B. Woodruff, Proc. Soc. Exptl. Biol. Med., 49, 207 (1942), streptolin, R. W. Rivett and W. H. Peterson, J. Amer. Chem. Soc., 69, 3006 (1947); racemomycins A, B, C and D, H. Taniyama, et al., Chem. Pharm. Bull., 19, 1627 (1971) and fucothricin, Hindustan Antibiot. Bull., 14, 4(1971). However, the antibiotic substances of this invention can be readily distinguished from the known antibiotics of this class by their different chromatographic behavior and acid hydrolysates, as well as spectral and other physical data. Furthermore, the complex 484-producing microorganism of this invention appears to be morphologically unique when compared to the known microorganisms capable of producing streptothricin and streptothricin-like antibiotics.

BRIEF SUMMARY OF THE INVENTION

The antibiotic substances of this invention are obtained by culturing a complex 484-producing organism in an aqueous nutrient medium under submerged aerobic fermentation.

The complex 484-producing organism, Streptomyces sp. NRRL 5490, was obtained from Easter Island soils and samples thereof have been deposited without restrictions with the Northern Utilization and Research Division, Agricultural Research Service, U.S. Department of Agriculture, Peoria, Ill., U.S.A.

It is to be understood that the invention is not limited to the use of the particular organism herein described, but includes variations and mutants obtained by natural selection or by treatment of the microorganism with, for instance, ultraviolet rays, X-rays, N-methyl-N'-nitro-N-nitroso-guanidine, manganese chloride, camphor, nitrogen mustards, and the like.

Streptomyces sp. NRRL 5490 develops abundantly in culture media usually employed for cultivation of other organisms of the same genus. It is capable of growing at temperatures ranging from 20° to 30°C, preferably at about 25° to 28°C, on Czapek's agar, oatmeal agar, nutrient agar, potato agar, glucose asparagine agar, glycerol asparagine agar, starch agar and peptone beef agar. Also, the organism grows very well on yeast extract agar, malt extract agar, starch-inorganic salts agar, oatmeal-tomato agar and Bennet's agar. The aerial mycelium is usually velvety or powdery and gray to pinkish gray in color and is spore forming. Sporophores are straight, sometimes spiral-shaped. Mycelial growth is light yellow to almost colorless and in some media pale brown. Occasionally a yellowish pigment is produced. The color of submerged mycelium ranges from yellow to rusty brown depending on the medium. The organism is $H_2S$-negative and melanine-negative.

Carbohydrate utilization by Streptomyces sp. NRRL 5490 was studied in carbon utilization agar (ISP Medium 9) according to the procedure standardized by the international Streptomyces Project (ISP).

Utilized carbohydrates included glucose, inositol, fructose, mannitol, rhamnose, xylose, starch and arabinose. Carbohydrates not utilized were sucrose, raffinose and cellulose.

The environment and nutritional requirements for the fermentation of Streptomyces sp. NRRL 5490 are similar to those necessary for the production of antibiotics by other aerobic microorganisms. Thus, aerobiosis is sustained in a liquid nutrient medium inoculated with a sterile culture incubated in flasks placed on shaking machines. For industrial production, metal tanks with internal aeration and agitation by means of paddles can be substituted. The microorganism requires as nutrient elements assimilable carbon and organic nitrogenous substances. The presence of mineral salts is desirable. Cultivation is best effected when the initial pH of the culture medium is between 5.5 and 7.5, the optimum pH being around 5.8 to 6.5.

The utilizable sources of assimilable carbon for the production of the antibiotic substances are very diverse, there being included sugars (for example, glucose, fructose, mannitol, maltose, arabinose, rhamnose, xylose, and the like, dextrin, starches of different types of origin, glycerol, inositol and other polyalcohols, and animal and vegetable fats, as well as esters thereof. The sources of organic assimilable nitrogen which actively stimulate growth and favor production of the antibiotic substances of this invention are substances such as soybean meal, cotton seed meal and other vegetable meals (whole or partially or totally defatted), meat flours or animal viscera, various peptones, casein hydrolysates, soybean hydrolysates, yeast hydrolysates, lactalbumin, wheat glutins, distillers solubles, corn steeps, molasses, urea and amino acids.

Mineral salts, such as the chlorides, nitrates, sulfates, carbonates and phosphates of sodium, potassium, ammonium and calcium, should be included in appropriate concentrations. The nutritive medium should contain a number of trace elements such as magnesium, iron, manganese and zinc.

The fermentation medium is inoculated with a spore suspension of the organism from a fresh slant culture of Streptomyces sp. NRRL 5490.

Under the described conditions and with the temperature of cultivation at about 20°–35°C, preferably at about 25° – 28°C, substantial production of the desired antibiotic complex is obtained. Maximum production usually occurs within the period of about two to nine days.

Thereafter, a variety of procedures may be employed in the isolation and purification of the antibiotic substances, for example, solvent extraction, partition chromatography, chromatography on a variety of absorbents, liquid-liquid distribution in a Craig apparatus, and crystallization from solvents.

The antibiotic substances of this invention are harvested in the following general manner:

The fermentation mixture is rendered acidic (pH 2 to 6, preferably about 3) by the addition of an acid. The mycelium is separated from the fermentation mixture by conventional means, such as filtration or centrifugation. The mycelium free fermentation mixture is adjusted to about pH 6.0 to 7.0, preferably pH 6.5. The mixture is then treated with an absorbent preferably by subjecting it to chromatography over a cation exchange resin, preferably one of the Amberlite IRC-50 type in the ammonium cycle. Other such resins include Zeokarb 226 and like carboxylic acid cation exchange resins. Thereafter, the antibiotic substances are eluted from the absorbent. In the case where the absorbent is one of the above cation exchange resins, elution is carried out with an alkaline solution, for example, ammonium hydroxide solution, or alkaline buffers, for example, ammonium acetate solution. The active fractions containing the antibiotic complex are combined to produce an extract from which the antibiotic complex is isolated. The complex can be further purified by precipitation from an appropriate solvent system to yield the purified antibiotic complex containing at least three components.

Thereafter, and if desired, the antibiotic complex is separated into various components by known separation techniques. Partition or absorption chromatography are convenient and efficient techniques for this purpose.

DETAILS OF THE INVENTION

For the purpose of this disclosure the term "antibiotic complex" is used to describe the total antibiotically active material isolable by the process of this invention. This material has been designated as Complex 484 and its characteristics are described in more detail hereinafter. The term "component" is used herein to describe a factor which is separated or isolated from the complex by known separation techniques. For convenience, individual components are arbitrarily designated 484-A, 484-B and the like. The term "antibiotic substances" is used herein to describe collectively the antibiotic complex and the components.

The antibiotic substances of this invention have useful antimicrobial activity. For example, they are useful against a broad spectrum of pathogenic bacteria.

The antibacterial activity of the antibiotic substances of this invention is demonstable in standard tests used for this purpose, for example, in the tests described in "Antiseptics, Disinfectants, Fungicides and Sterilization", G. F. Reddish, Ed., second ed., Lea and Febiger, Philadelphia, 1957 or by D. C. Grove and W. A. Randall in "Assay Methods of Antibiotics", Med. Encycl. Inc., New York 1955.

For example, by employing a test like the serial broth dilution, see Reddish, cited above, in which dilutions of the antibiotic substances of this invention in nutrient broth are inoculated with the microorganisms, incubated at 37°C for 2 days, respectively, and examined for the presence of growth, it was shown that the antibiotic substances inhibit growth totally of a variety of pathogenic microorganisms. The results of such an experiment are reported hereinafter.

When the antibiotic substances of this invention are employed as antibacterial agents in warm-blooded animals, e.g. rats, they are used alone or in combination with pharmaceutically acceptable carriers, the proportion of which is determined by the solubility and chemical nature of the compound, chosen route of administration and standard biological practice. For example, an antibacterially effective amount of the substance is administered orally in solid form containing such excipients as starch, sugar, certain types of clay and so forth. Similarly, such an amount can also be administered orally in the form of solutions or suspensions, or the antibiotic substance is injected parenterally. For parenteral administration the substance is used in the form of a sterile solution or suspension containing other solutes or suspending agents, for example enough saline or glucose to make the solution isotonic, bile salts, acacia, gelatin, sorbitan monoleate, polysorbate 80 (oleate esters of sorbital and its anhydrides copolymerized with ethylene oxide) and the like.

The dosage of the antibiotic substances will vary with the form of administration and the particular substance chosen Furthermore, it will vary with the particular host under treatment. Generally, treatment is initiated with small dosages substantially less than the optimum dose of the substance. Thereafter, the dosage is increased by small increments until the optimum effect under the circumstances is reached. In general, the antibiotic substances of this invention most desirably administered at a concentration level that will generally afford antibacterially effective results without causing any harmful or deleterious side effects and preferably at a level that is in a range of from about 1.0 mg to about 250 mg per kilo per day, although as aforementioned variations will occur. However, a dosage level that is in the range of from about 10 mg to about 100 mg per kilo per day is most desirably employed in order to achieve effective results.

In addition, the antibiotic substances may be employed topically. For topical application they are formulated in the form of solutions, creams or lotions in pharmaceutically acceptable vehicles containing 0.1 − .5 percent, preferably 2 percent of the antibiotic substances and are administered topically to the infected area of the skin.

The antibiotic substances can also be used for cleaning and disinfecting laboratory equipment, surgical instruments, locker rooms, or shower rooms. For such purposes it is preferred to use 0.1 − 10% solutions of the substances in water.

Preparation

In a preferred embodiment of this invention the antibiotic substances are obtained in the following manner:

A suitable fermenter is charged with a production medium (see Example 1). After sterilization and cooling, the medium is inoculated with a first stage inoculum preparation of Streptomyces sp. NRRL 5490.

The fermentation is allowed to proceed at 20° to 35°C, preferably 25° to 28°C. During the course of the fermentation the pH of the fermentation mixture is kept between 5.5 to 7.5, preferably 5.8 to 6.5 by the addition of a base, for example, 25% sodium, potassium or preferably ammonium hydroxide solution.

After about 2 to 9 days, usually about 6 days, a maximum titre of the antibiotic substances of this invention is usually obtained. The concentration of the antibiotic substances in the fermentation mixture is readily followed during the course of the fermentation by testing samples of the mixture for their inhibitory effect of a strain of Pseudomonas aeruginosa or Sarcina lutea as determined by the cup plate method.

Thereafter the fermentation is stopped, and the pH of the mixture adjusted to about 3 with an acid, for example, sulfuric or hydrochloric acid. The mycelium is separated from the fermentation mixture by subjecting the mixture to filtration through a filter aid, for example, diatomaceous earth. The filtrate, i.e. the mycelium-free fermentation mixture, is adjusted to about pH 6.0 to 7.0, preferably 6.5, by the addition of base, for example, 1 N ammonium hydroxide or sodium hydroxide solution. The adjusted filtrate is now subjected to chromatography on a cation exchange resin, for example Amberlite IRC-50 in the ammonium cycle, in an amount equal in volume to 1/10 to 1/30 the volume of the filtrate. Accordingly, the filtrate is passed through the exchange resin whereby the antibiotic substances are absorbed on the resin. The resin is then washed with distilled water and eluted with an alkaline solution preferably ammonium hydroxide (0.25 to 1 N, pH = 11.4 to 11.8). The eluate is concentrated, preferably at reduced pressure at temperatures between 35° to 60°C. The residue is dissolved in about 50 parts (w/v) of a solvent of moderate polarity, for example water, a lower alkanol or mixtures thereof. The solution is treated with decolorizing charcoal, filtered and the collected charcoal washed with about 10 to 20 parts of the same solvent. The combined filtrate and washing are concentrated to about one-tenth of their original volume. The concentrated solution is treated with about five to ten times its volume of a diluent of low polarity, miscible with the above solvent of moderate polarity, for example, acetone or methyl ethyl ketone in the case where water is the above solvent of moderate polarity, or acetone, methyl ethyl ketone, ether or ethyl acetate in the case where a lower alkanol is the solvent of moderate polarity. The resulting precipitate is collected affording the crude antibiotic complex of this invention. A preferred combination of moderate and low polarity solvents for the foregoing procedure is a lower alkannol and a lower alkanone, respectively; for example, methanol/acetone, methanol/methyl ethyl ketone, and the like.

Further purification of the crude antibiotic complex is obtained by dissolving and reprecipitating the antibiotic complex from the aforementioned solvent system of moderate and low polarity solvents.

If desired, the antibiotic complex is separated into various components. This separation is effected by further subjection the complex to chromatography. A convenient and efficient absorbent for the chromatographic separation is a cross-linked dextran cation exchanger of the CM-Sephadex type, preferably CM-Sephadex C-25. Other suitable absorbents include silica gel, dextran gel, weak cation exchange resins, activated carbon, cellulose powder or cellulose based cation exchangers, e.g. carboxymethyl cellulose.

When the CM-Sephadex is used as the absorbent, stepwise elution of the various antibiotic components is effected by using a volatile buffer, generally ammonium acetate or dilute ammonium hydroxide, and a gradient of pH 7 to about 11.4 for elution.

By means of the chromatographic separation the antibiotic complex 484 is separated into at least two components which are arbitrarily designated as 484-A and 484-B.

More specifically, the components are readily obtained by subjecting the antibiotic complex to chromatography on silica gel, activated carbon, cellulose powder, weak cation exchange resins, for example Amberlite IRC-50 (Rohm & Haas Co.), cellulose based cation exchangers, for example, carboxymethyl cellulose and crosslinked dextran based cation exchangers (Sephadex ion exchangers), for example, CM-Sephadex (Pharmacia Co.). The preceding ion exchangers can also be used in a batch treatment. Purification may also be done by gel filtration on dextran gels such as Sephadex G-10, G-15 and 1H-20 (Pharmacia) or acrylamide gels (Bio-Rad).

The ion exchangers are prepared according to the instructions of the manufacturer in water or suitable buffers preferably volatile buffers such as pyridine-acetic acid, ammonium acetate or ammonium formate. Elution is carried out with dilute acid, dilute alkali or suitable buffers, preferably volatile buffers such as ammonium acetate employing if necessary a gradient of pH or ionic concentration or a gradient of pH and ionic concentration.

A preferred separation procedure includes chromatography on CM-Sephadex C-25. The ion exchanger in the $NH_4^+$ form is equilibrated to a pH of about 5.0 to 8.0, preferably pH 7.0, using dilute ammonium acetate, preferably 0.05 N. Elution of the column is initiated using dilute ammonium acetate as the buffer. The pH of the buffer is adjusted with acetic acid or ammonium hydroxide. The material eluted by buffers up to pH 10.0 is inactive or slightly active. Buffer of pH 10.5 elutes the most polar material with a more favourable ratio of antibacterial activity to toxicity than the antibiotic complex. This component is arbitrarily assigned the designation 484-A. The latter component is dissolved in aqueous lower alkanol, preferably methanol-water (1:1) and the solution poured through a column of a weak base anion exchange resin, for example, Amberlite IR-45 and IR-4B, De-Acidite E, Duolite A-2 and the like. The eluate is concentrated to dryness to afford the component substantially free of inorganic ions (i.e. ammonium and acetate ions). Additional purification of this component, 484-A, is achieved by dissolving and reprecipitating the component in the aforementioned solvent system described for additional purification of the antibiotic complex. This purified component 484-A is more fully described hereinafter.

Having substantially eluted component 484-A as described above, further elution of the column with buffer of pH 10.5 and with 0.25 N ammonium hydroxide (i.e. an alkaline solution of about pH 11.4) gives material containing, along with a small amount of component 484-A, a less polar fraction as indicated by thin layer chromatography. This material is arbitrarily designated component 484-B. This latter component possesses a higher degree of both antibacterial activity and toxicity than the antibiotic complex 484. If desired additional purification of the component is achieved in the same manner as described above for component 484-A. Furthermore, thin layer chromatography on silica gel plates using methanol-chloroform-28% ammonia (2:1:2) as the mobile phase indicates that component 484-B is a mixture of two or more fractions (Rf's 0.18 and 0.36). This component is described in more detail hereinafter.

Characterization of Antibiotic Complex 484

The composition of Complex 484 has indefinite physical constants such as melting point, analytical values and specific rotation because the ratio of various components therein varies with the conditions of fermentation and/or extraction of the complex. However, the complex has a specific rotation ($[\alpha]_D^{25}$) of $-25° \pm 3°$ (methanol), i.e. the specific rotation of several batches ranges from $-22°$ to $-28°$ (methanol). For example, on batch had a specific rotation, $[\alpha]_D^{25} = -24.8°$ (methanol).

Notwithstanding, the complex is characterized readily by its mode of preparation and its subsequent separation into the various components described herein.

Additional characterization includes:

a. The complex is soluble in water and methanol and substantially insoluble in non polar and moderately non polar solvents, such as acetone, ether, benzene, ethyl acetate and chloroform.

b. The complex is convertible to acid addition salts, for example, the inorganic acid addition salts, hydrochloride, hydrobromide, sulfate and phosphate, and the organic acid addition salts, for example, acetate, pyruvate, tartrate, citrate, malate an aspartate. The salts are readily obtained by treating the complex with the corresponding organic or inorganic acid. The salts possess the same antibacterial activity as the complex itself and are used in the same manner.

c. Paper chromatography of the complex in the conventional descending manner at 24°C for 48 hours on Whatman No. 1 paper using a solvent system consisting of n-propanol, pyridine, acetic acid and water (30:20:6:20) gives mainly two areas of antimicrobial activity, as determined by bioautography on agar plates seeded with Sarcina lutea, 25 and 11 cm from the origin.

d. The complex does not exhibit any characteristic absorption between 220 and 350 nm in its ultraviolet absorption spectrum (95% ethanol).

e. A representative infrared absorption spectrum of the complex in KBr pellet is reproduced in accompanying FIG. 1 and shows characteristic absorption bands at 3330, 2925, 2875 (sh), 1710, 1650, 1560 (sh), 1450, 1380, 1170, 1080, 1030, 970, 920 and 820 cm$^{-1}$.

f. The minimum inhibitory concentration of the antibiotic complex against various microorganisms are listed in Table 1 below.

g. The complex exhibits a LD$_{50}$ (i.p., mice) ranging from 350 to 450 mg/kg and a LD$_0$ (p.o., mice) of $> 1.0$ g/kg.

In protection studies mice were infected with *E. coli* ATCC 10536. At one hour and again at five hours after infection, mice were administered 20 mg/kg (s.c.) of the antibiotic complex 484. At this dose 50% of these mice were protected. At 25 mg/kg all the mice were protected.

Furthermore, the complex gives a positive reaction to ninhydrin, a yellow color with Elson-Morgan reagent (i.e. a negative reaction), a negative reaction with Sakaguchi reagent and a positive reaction with silver nitrate reagent.

Characterization of Antibiotic Component 484-A

Component 484-A is characterized by its mode of preparation and the following additional characterization:

a. Component 484-A, similar to the complex 484, is soluble in water and methanol and substantially insoluble in acetone, ether, benzene, ethyl acetate and chloroform.

b. Component 484-A is convertible to acid addition salts, for example the inorganic acid addition salts, hydrochloride, hydrobromide, sulfate and phosphate, and the organic acid addition salts, for example, acetate, pyruvate, tartrate, citrate, malate and aspartate. The salts are readily obtained by treating the component with the corresponding organic or inorganic acid. The salts possess the same antibacterial activity as the component itself and are used in the same manner.

c. Paper chromatography of component 484-A in the conventional descending manner at 24°C for 48 hours an Whatman No. 1 paper using a solvent system consisting of n-propanol, pyridine, acetic acid and water (30:20:6:20) gives one main zone of antimicrobial activity (23 - 25 cm. from origin) as shown by bioautography on plates seeded with *Sarcina lutea*. When the duplicate paper chromatograms are sprayed with ninhydrin two main spots (13 - 15 cm and 23 - 25 cm from origin) are detected. The sulfate salt of component 484-A under the above conditions of descending chromatography and bioautography shows one bioactive zone about 18 to 20 cm from origin. Ninhydrin spray reveals two spots (10 cm and 18 - 20 cm from origin). Racemomycin A sulfate, H. Taniyama and F. Miyoshi, Chem. Pharm. Bull. (Tokyo), 10, 156 (1962), a known streptothricin-like antibiotic used as a standard, shows a wide zone of inhibition 21 - 26 cm. from origin when tested under the same conditions and a duplicate chromatogram sprayed with ninhydrin reveals a spot at 24 cm.

d. Paper chromatography of the sulfate salt of component 484-A in the conventional ascending manner at 24°C for 16 hours on Whatman No. 1 paper using a solvent system consisting of n-propanol, pyridine, acetic acid and water (30:20:6:24) gives two main spots as detected by ninhydrin Rf 0.15 - 0.16 and Rf 0.22 - 0.24; Racemomycin A sulfate gives a spot with Rf 0.23 - 0.24 under these conditions.

e. Circular paper chromatography [see, M. I. Horowitz and C. P. Schaffner, Anal. Chem., 30 1616 (1958)], of the sulfate salt of component 484-A using Whatman No. 1 paper and a solvent system consisting of n-propanol, pyridine, acetic acid and water (30:20:6:24) gives one zone of antimicrobial activity at Rf 0.40 - 0.42 and two zones with Rf 0.30 - 0.32 and Rf 0.40 - 0.42 as detected by ninhydrin spray; racemomycin A sulfate gives a spot with Rf 0.44 - 0.46 in this system as detected by ninhydrin spray.

f. A representative infrared absorption spectrum of component 484-A in KBr pellet is reproduced in the accompanying FIG. 2 and shows characteristic absorption bands at 3300, 3080 (sh), 2940 (sh), 1710 (sh), 1660, 1550, 1390, 1350, 1310, 1105, 955, 920 and 850 cm$^{-1}$.

g. The minimum inhibitory concentration of component 484-A against various microorganisms is listed in Table 1, see below.

h. Component 484-A exhibits a LD$_{50}$ (i.p., mice)$>1.0$ g/kg. This LD$_{50}$ readily distinguishes this substance from other known streptothricin-like antibiotics.

i. Amino acid analysis of component 484-A indicated the presence of a streptolidine moiety and a L-$\beta$-lysine moiety in about a 1 to 1 ration.

In protection studies mice were infected with *E. coli* ATCC 10536. At 1 hour and again at 5 hours after infection, mice were given 25 mg/kg, (s.c) of component 484-A. The result was complete protection of the mice.

Furthermore, like the complex, component 484-A gives positive reactions with ninhydrin and silver nitrate, and negative reactions with Elson-Morgan and Sakaguchi reagents.

The specific rotation ($[\alpha]_D^{25}$) of component 484-A is $-25° \pm 3°$ (H$_2$O), i.e. the specific rotation of several batches range from $-22°$ to $-28°$ (H$_2$O). One sample of component 484-A had the specific rotation $[\alpha]_D^{25} = -27°C$ (H$_2$O).

The specific rotation ($[\alpha]_D^{25}$) of several batches of component 484-A ranges from $-22°$ to $-28°$ (H$_2$O). One sample of component 484-A had the specific rotation $[\alpha]_D^{25} = -27°C$ (H$_2$O).

Characterization of Antibiotic Component 484-B

Component 484-B is characterized by its mode of preparation and the following additional characterization:

a. Component 484-B, like the complex 484 and the component 484-A, is soluble in water and methanol and substantially insoluble in acetone, ether, benzene, ethyl acetate and chloroform.

b. Component 484-B is convertible to acid addition salts, for example, the inorganic acid addition salts, hydrochloride, hydrobromide, sulfate and phosphate, and the organic acid addition salts, for example, acetate, pyruvate, tartrate, citrate, malate and aspartate. The salts are readily obtained by treatment of the component with the corresponding organic or inorganic acid. The salts possess the same antibacterial activity as the component itself and are used in the same manner.

c. Paper chromatography of the component 484-B in the conventional descending manner at 24°C for 48 hours on Whatman No. 1 paper using a solvent system consisting of n-propanol, pyridine, acetic acid and water (6:4:1.5:4) gives a main area of antimicrobial activity, as determined by bioautography on agar plates seeded with *Sarcina lutea*, at 17 cm and minor zones at 24 and 8 cm from the origin.

d. Circular chromatography utilizing Whatman No. 1 paper and a solvent system consisting of n-propanol, pyridine, acetic acid and water (30:20:6:24) gives three zones as detected by ninhydrin (Rf 0.16, 0.29 and 0.42).

e. A representative infrared absorption spectrum of component 484-B is reproduced in accompanying FIG. 3 and shows characteristic bands at 3280, 3070, 2930, 1710, 1655, 1550, 1395, 1075 and 920 cm$^{-1}$.

f. The minimum inhibitory concentration of component 484-B against various microorganisms as listed in Table 1, see below.

g. Component 484-B exhibits a LD$_{50}$ (i.p., mice) of about 100 mg/kg.

h. Amino acid analysis of component 484-B indicates the presence of a streptolidine moiety and a L-$\beta$-lysine moiety in about a 1 to 2 ratio.

The specific rotation ($[\alpha]_D^{25}$) of this component is $-12° \pm 2°$ (H$_2$O), i.e. the specific rotation of several batches of component 484-A ranged from $-10°$ to $-14°$ (H$_2$O). One sample of component 484-B had a specific rotation, $[\alpha]_D^{24} = -12°$ (H$_2$O).

TABLE I

| | Minimum Inhibitory Concentration (MIC) in mcg/ml for the Antibiotic Substances of this Invention | | |
|---|---|---|---|
| Test Microorganism | Complex 484 | Component 484-A | Component 484-B |
| *Staphylococcus pyogenes* (penicillin-sensitive) | 0.4 | 0.8 | <0.1 |
| *Staphylococcus pyogenes* (penicillin-resistant) | 3.2 | 3.2 | 0.4 |
| *Streptococcus faecalis* | 50.0 | 50.0 | 12.5 |
| *Escherichia coli* | 3.2 | 3.2 | 0.8 |
| *Aerobacter aerogenes* | 1.6 | 1.6 | 0.4 |
| *Salmonella pullorum* | 50.0 | 50.0 | 6.4 |
| *Pseudomonas aeruginosa* | 50.0 | 50.0 | 12.5 |
| *Proteus mirabilis* | 3.2 | 3.2 | 0.8 |
| *Proteus vulgaris* | 1.6 | 3.2 | 0.4 |
| *Klebsiella pneumoniae* | 1.6 | 1.6 | 0.4 |
| *Serratia marcescens* | 3.2 | 3.2 | 0.8 |

The following examples illustrate further this invention.

EXAMPLE 1

Preparation and Purification of Complex 484

Microorganism

Steptomyces sp. NRRL 5490 was grown and maintained on oatmeal-tomato paste agar slants (T.G. Pridham, et al., Antibiotic Annual 1956 – 1957, Medical Encyclopedia Inc., New York, p. 947) and in Roux bottles containing the same medium. Good growth was obtained after 7 days of incubation at 28°C. Spores from one Roux bottle were washed off and suspended into 50 ml of sterile distilled water. This suspension was used to inoculate the first stage inoculum.

First Stage Inoculum

The first stage inoculum medium is an aqueous medium having the following constituents:

| | |
|---|---|
| glucose (Cerelose) | 2.0% |
| peptone (Neopeptone) | 0.5% |
| tomato paste | 1.0% |
| corn meal | 0.8% |
| "Blackstrap" molasses | 2.0% |
| sodium chloride | 0.3% | pH adjusted to 7.8 with ammonium hydroxide

This first stage inoculum medium (3.2 l), contained in a 24 liter Florence flask, was sterilized at 121°C for 1 hour, cooled and inoculated with (32 ml, 1% inoculum) of the spore suspension described above. The inoculated flask was incubated for 30 hours at 28°C on a reciprocating shaker operating at 65 rev/min (4 inches-stroke).

Production Stage

The production stage was run in 250 liter New Brunswick fermenters, Model F-250, equipped with automatic antifoam addition system and pH recorder-controller. The fermenters were charged with 160 liters of the same medium as described above, and lard oil (0.1% v/v, Larex No. 1, Swift Canadian Co., Toronto) was added as an antifoam agent before sterilization. The fermenters were sterilized at 121°C for 35 minutes. The sterilized and cooled fermenters were inoculated with one flask (3.2 l, 2% inoculum) of first stage inoculum. Incubation temperature: 28°C; aeration: 0.5 vol/vol/min; agitation: 250 rev/min. The antifoam agent, used on demand, was Mazur DF-143PX (Mazur Chemical Corp., Gurnee, Illinois). During the course of fermentation pH was kept at or above 6.0 by automatic addition of 25% sodium hydroxide solution.

After six days incubation the pH of the fermentation broth reached 7.5 and a 1.3 cm diameter filter paper disc in broth gave an inhibition zone of 23 mm on an agar plate seeded with a strain of Pseudomonas aeruginosa. At this time the packed cell volume (PCV) was 24%. The fermentation was stopped, the pH of the broth was adjusted to 3.0 with sulfuric acid, and diatomaceous earth (5% v/v) was added. The mixture was subjected to filtration. The filtrate containing the antibiotic principle was retained and the mycelium discarded.

Extraction and Recovery

The pH of the filtrate (volume = 150 liters) was adjusted to 6.5 with 1 N ammonium hydroxide solution. The filtrate was passed through a column containing 7 liters of Amberlite IRC 50 $NH_4^+$ resin at a rate of 20 liters per hour. The product was absorbed on the resin and the eluate was rejected. The resin was washed with deionized water until the washings were colorless. The product was eluted from the resin with 12 liters of 1 N ammonium hydroxide solution. The ammonium hydroxide eluate was evaporated to dryness under reduced pressure at 40°C. The residue was dissolved in 3 liters of methanol with vigorous stirring. The solution was filtered. The filtrate containing the active principle was decolorized by stirring for 20 min. with 1% charcoal (Darco G-60) and filtered. The charcoal was washed with 1 liter of methanol with stirring. The methanol filtrate and washings were evaporated to 500 ml under reduced pressure. Addition of 7 volumes of acetone to the methanol concentrate precipitated the antibiotic complex.

Further purification was obtained by dissolving the latter product (40 g) in 400 ml. of methanol and slowly adding 2800 ml of acetone to the vigorously stirred solution. The resulting precipitate was collected. Repetition of this purification step gave the purified complex.

EXAMPLE 2

Separation of the Complex 484 into Components 484-A and 484-B.

CM-Sephadex C-25 in the $NH_4^+$ form was equilibrated with 0.05 N ammonium acetate (pH 7). The complex (10.0 g), obtained as described in Example 1, was dissolved in a small volume of water and the pH adjusted to 7 with acetic acid. This solution was applied to a column containing 300 ml of the above ion exchanger, CM-Sephadex C-25. The column was eluted stepwise with buffered 0.05 M ammonium acetate of increasing pH, the pH being adjusted by the addition of ammonium hydroxide or acetic acid. The eluted fractions were evaporated to dryness under reduced pressure. Accordingly, the column was eluted first with 2 – 3 bed volumes of ammonium acetate buffer (pH 7), followed by 2 – 3 bed volumes of ammonium acetate buffer (pH 9.0). These fractions were inactive and were discarded. The column was eluted next with 3 – 4 bed volumes of ammonium acetate buffer (pH 10). The material obtained had a low order of activity. Thereafter the column was eluted with 3 – 4 bed volumes of ammonium acetate buffer (pH 10.5). The first 1 – 1.5 bed volumes of eluate contained material of low activity and the next 1 – 2 bed volumes contained material of high activity. This material was designated component 484-A.

Further elution of the column with the same buffer (3rd and 4th bed volumes), followed by elution with 2 – 3 bed volumes of 0.25 N ammonium hydroxide gave material of high activity. This material was designated component 484-B.

Component 484-A or 484-B were purified further by dissolving each component in a small volume of 50% methanol-water and passing the solution through a column of Amberlite IR-45 ($OH^-$). The resulting precipitate was collected, washed with acetone and dried under reduced pressure to give the purified components 484-A and 484-B, respectively.

Elementary analysis of component 484-A indicates an empirical formula containing from 1 – 3 molecules of water per molecule of free base, viz., $C_{18-19}H_{34-36}N_{7-8}O_{7-8} \times 1 - 3\ H_2O$. The hydrochloride salt of component 484-A contains from 1 – 3 molecules of water and from 1 – 3 molecules of hydrochloric acid per molecule of free base, viz., $C_{18-19}H_{34-36}N_{7-8}O_{7-8} \times 1-3\ H_2O \times 1-3\ HCl$.

Elementary analysis of component 484-B indicates an empirical formula containing from 1 – 5 molecules of water per molecule of free base, viz., $C_{23-25}H_{44-46}N_{9-10}O_{8-9} \times 1-5\ H_2O$.

We claim:

1. A pharmaceutical composition for inhibiting the growth of pathogenic bacteria in a mammal which comprises a pharmaceutical carrier and an effective antibacterial amount of the antibiotic component 484A, which antibiotic component 484A
    a. is soluble in water and methanol and substantially insoluble in acetone, ether, benzene, ethyl acetate and chloroform,
    b. is convertible to acid addition salts,
    c. gives one main zone of antimicrobial activity at 23 – 25 cm from origin on descending paper chromatography at 24°C for 48 hours on Whatman No. 1 paper using a solvent system consisting of n-propanol, pyridine, acetic acid and water (30:20:6:20) and two main spots 13 – 15 cm and 23 – 25 cm from origin in the same system as revealed by ninhydrin spray,
    d. is convertible to a sulfate salt giving two main spots, Rf 0.15 – 0.16 and Rf 0.22 – 0.24 on ascending paper chromatography at 24°C for 16 hours on Whatman No. 1 paper using a solvent system consisting of n-propanol, pyridine, acetic acid and water (30:20:6:24) as detected by ninhydrin, e. is convertible to a sulfate salt giving two zones, as detected by ninhydrin spray, Rf 0.30 – 0.32 and Rf 0.40 – 0.42 on circular paper chromatography using Whatman No. 1 paper and a solvent system consisting of n-propanol, pyridine, acetic acid and water (30:20:6:24) and in the same system gives one zone of antimicrobial activity at Rf 0.40 – 0.42, f. has a representative infrared absorption spectrum in KBr pellet as shown in accompanying FIG. 2, showing bonds at 3300, 3080 (sh), 2940 (sh), 1710 (sh), 1660, 1550, 1390, 1310, 1105, 955, 920, and 850 cm$^{-1}$, g. inhibits growth of *Staphylococcus pyrogenes* (penicillin-sensitive), *Staphylococcus pyogenes* (penicillin-resistant), *Streptococcus faecalis*, *Escherichia coli*, *Aerobacter aerogenes*, *Salmonella pullorum*, *Pseudomonas aeruginosa*, *Proteus mirabilis*, *Proteus vulgaris*, *Klebsiella pneumoniae* and *Serratia marcescens*, h. exhibits a LD$_{50}$ (i.p., mice) mice) of 1.0 g/kg, i. has about a 1 to 1 ratio of streptolidine and L-β-lysine moieties as indicated by amino acid analysis, j. has a specific rotation, $[\alpha]_D^{25} = -25° \pm 3°$ (H$_2$O), k. gives positive reaction with ninhydrin and silver nitrate and negative reactions with Elson-Morgan and Sakaguchi reagents, and l. has an empirical formula C$_{18-19}$H$_{34-36}$N$_{7-8}$O$_{7-8}$× 1–3 H$_2$O.

Figure 3:
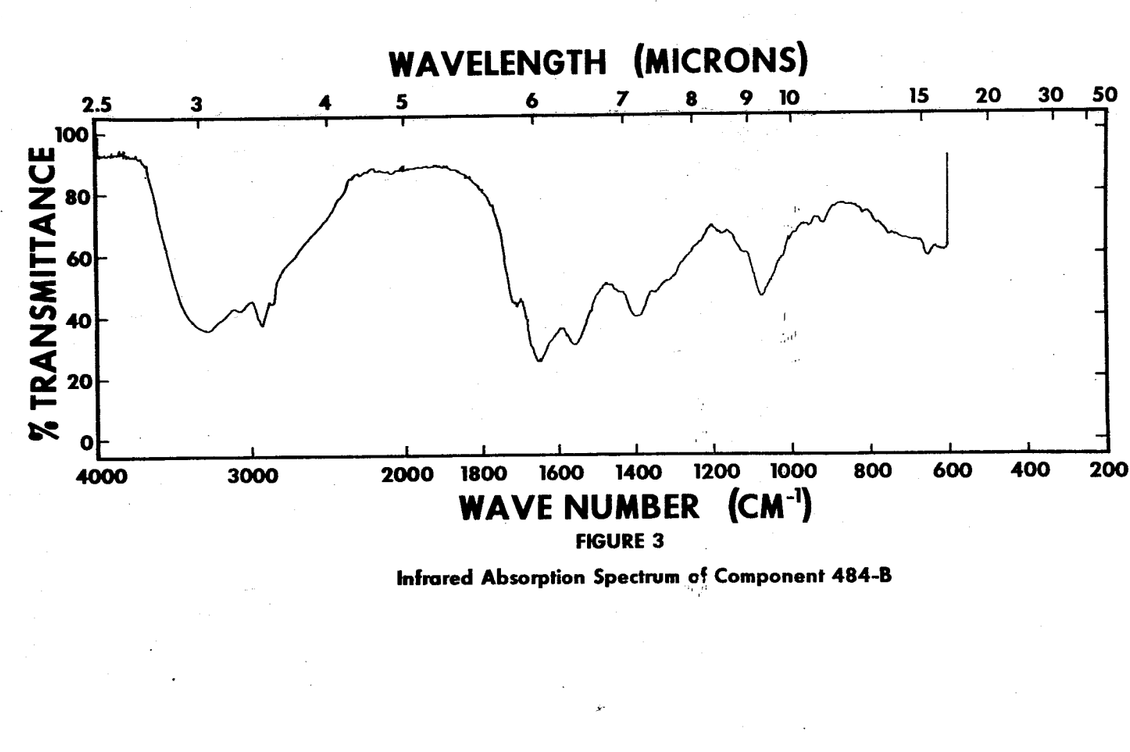

2. A pharmaceutical composition for inhibiting the growth of pathogenic bacteria in a mammal which comprises a pharmaceutical carrier and an effective antibacterial amount of the antibiotic component 484B, which antibiotic component 484B a. is soluble in water and methanol and substantially insoluble in acetone, ether, benzene, ethyl acetate and chloroform, b. is convertible to acid addition salts, c. gives a main area of antimicrobial activity at 17 cm and minor areas at 24 and 8 cm from the origin on descending paper chromatography at 24°C for 48 hours on Whatman No. 1 paper using a solvent system consisting of n-propanol, pyridine, acetic acid and water (6:4:1.5:4), d. gives three zones, as detected by ninhydrin spray, Rf 0.16, 0.29 and 0.42, on circular paper chromatography using Whatman No. 1 paper and a solvent system consisting of n-propanol, pyridine, acetic acid and water (30:20:6:24), e. has a representative infrared absorption spectrum in KBr pellet as shown in accompanying FIG. 3, showing bands at 3280, 3070, 2930, 1710, 1655, 1550, 1395, 1075 and 920 cm$^{-1}$, f. inhibits the growth of *Staphylococcus pyogenes* (penicillin-sensitive), *Staphylococcus pyogenes* (penicillin-resistant), *Streptococcus faecalis*, *Escherichia coli*, *Aerobacter aerogenes*, *Salmonella pullorum*, *Pseudomonas aeruginosa*, *Proteus mirabilis*, *Proteus vulgaris*, *Klebsiella pneumoniae* and *Serratia marcescens*, g. exhibits a LD$_{50}$ (i.p., mice) of about 100 mg/kg, h. has about a 1 to 2 ratio of streptolidine and L-β-lysine moieties as indicated by amino acid analysis, i. has a specific rotation, $[\alpha]_D^{24} = -12° \pm 2°$ (H$_2$O), and j. has as an empirical formula C$_{23-25}$H$_{44-46}$N$_{9-10}$O$_{8-9}$×1–5 H$_2$O.

3. A method of inhibiting the growth of pathogenic bacteria in a mammal which comprises administering to said mammal an effective antibacterial amount of the antibiotic component 484A which a. is soluble in water and methanol and substantially insoluble in acetone, ether, benzene, ethyl acetate and chloroform, b. is convertible to acid addition salts, c. gives one main zone of antimicrobial activity at 23 – 25 cm from origin on descending paper chromatography at 24°C for 48 hours on Whatman No. 1 paper using a solvent system consisting of n-propanol, pyridine, acetic acid and water (30:20:6:20) and two main spots 13 – 15 cm and 23 – 25 cm from origin in the same system as revealed by ninhydrin spray, d. is convertible to a sulfate salt giving two main spots, Rf 0.15 – 0.16 and Rf 0.22 – 0.24 on ascending paper chromatography at 24°C for 16 hours on Whatman No. 1 paper using a solvent system consisting of n-propanol, pyridine, acetic acid and water (30:20:6:24) as detected by ninhydrin, e. is convertible to a sulfate salt giving two zones, as detected by ninhydrin spray, Rf 0.30 – 0.32 and Rf 0.40 – 0.42 on circular paper chromatography using Whatman No. 1 paper and a solvent system consisting of n-propanol, pyridine, acetic acid and water (30:20:6:24) and in the same system gives one zone of antimicrobial activity at Rf 0.40 – 0.42, f. has a representative infrared absorption spectrum in KBr pellet as shown in accompanying FIG. 2, showing bonds at 3300, 3080 (sh), 2940 (sh), 1710 (sh), 1660, 1550, 1390, 1310, 1105, 955, 920, and 850 cm$^{-1}$, g. inhibits growth of *Staphylococcus pyrogenes* (penicillin-sensitive), *Staphylococcus pyogenes* (penicillin-resistant), *Streptococcus faecalis*, *Escherichia coli*, *Aerobacter aerogenes*, *Salmonella pullorum*, *Pseudomonas aeruginosa*, *Proteus mirabilis*, *Proteus vulgaris*, *Klebsiella pneumoniae* and *Serratia marcescens*, h. exhibits a LD$_{50}$ (i.p., mice) of 1.0 g/kg, i. has about a 1 to 1 ratio of streptolidine and L-β-lysine moieties as indicated by amino acid analysis, j. has a specific rotation, $[\alpha]_D^{25} = -25° \pm 3°$ (H$_2$O), k. gives positive reaction with ninhydrin and silver nitrate and negative reactions with Elson-Morgan and Sakaguchi reagents, and l. has an empirical formula C$_{18-19}$H$_{34-36}$N$_{7-8}$O$_{7-8}$×1–3 H$_2$O.

4. A method of inhibiting the growth of pathogenic bacteria in a mammal which comprises administering to said mammal an effective antibacterial amount of the antibiotic component 484B which a. is soluble in water and methanol and substantially insoluble in acetone, ether, benzene, ethyl acetate and chloroform, b. is convertible to acid addition salts, c. gives a main area of antimicrobial activity at 17 cm and minor areas at 24 and 8 cm from the origin on descending paper chromatography at 24°C for 48 hours on Whatman No. 1 paper using a solvent system consisting of n-propanol, pyridine, acetic acid and water (6:4:1.5:4), d. gives three zones, as detected by ninhydrin spray, Rf 0.16, 0.29 and 0.42, on circular paper chromatography using Whatman No. 1 paper and a solvent system consisting of n-propanol, pyridine, acetic acid and water (30:20:6:24), e. has a representative infrared absorption spectrum in KBr pellet as shown in accompanying FIG. 3, showing bands at 3280, 3070, 2930, 1710, 1655, 1550, 1395, 1075 and 920 cm$^{-1}$, f. inhibits the growth of *Staphylococcus pyogenes* (penicillin-sensitive), *Staphylococcus pyogenes* (penicillin-resistant), *Streptococcus faecalis*, *Escherichia coli*, *Aerobacter aerogenes*, *Salmonella pullorum*, *Pseudomonas aeruginosa*, *Proteus mirabilis*, *Proteus vulgaris*, *Klebsiella pneumoniae* and *Serratia marcescens*, g. exhibits a LD$_{50}$ (i.p., mice) of about 100 mg/kg, h. has about a 1 to 2 ratio of streptolidine and L-$\beta$-lysine moieties as indicated by amino acid analysis, i. has a specific rotation, $[\alpha]_D^{24} = -12° \pm 2°$ (H$_2$O), and j. has an empirical formula C$_{23-25}$H$_{44-46}$N$_{9-10}$O$_{8-9}$×1–5 H$_2$O.

* * * * *